US012433767B2

(12) United States Patent
Goldberg et al.

(10) Patent No.: US 12,433,767 B2
(45) Date of Patent: Oct. 7, 2025

(54) SYSTEMS AND METHODS FOR CONTROLLED FACET REPOSITIONING IN THE CALCANEUS

(71) Applicant: Paragon 28, Inc., Englewood, CO (US)

(72) Inventors: Andrew Julian Goldberg, Radlett (GB); Richard Matthew Obert, Poway, CA (US); Mathew Richard Anderle, Greenwood Village, CO (US)

(73) Assignee: Paragon 28, Inc., Englewood, CO (US)

(*) Notice: Subject to any disclaimer, the term of this patent is extended or adjusted under 35 U.S.C. 154(b) by 825 days.

(21) Appl. No.: 17/657,522

(22) Filed: Mar. 31, 2022

(65) Prior Publication Data

US 2022/0313453 A1 Oct. 6, 2022

Related U.S. Application Data

(60) Provisional application No. 63/170,174, filed on Apr. 2, 2021.

(51) Int. Cl.

| | |
|---|---|
| ***A61F 2/46*** | (2006.01) |
| ***A61B 17/15*** | (2006.01) |
| ***A61B 34/10*** | (2016.01) |
| ***A61F 2/42*** | (2006.01) |
| *A61F 2/30* | (2006.01) |

(52) U.S. Cl.

CPC .......... *A61F 2/4606* (2013.01); *A61B 17/152* (2013.01); *A61B 34/10* (2016.02); *A61B 2034/108* (2016.02); *A61F 2002/30266* (2013.01); *A61F 2002/4217* (2013.01)

(58) Field of Classification Search

CPC ........... A61F 2002/4217; A61F 2/4202; A61B 17/152; A61B 2017/568; A61B 2034/108

See application file for complete search history.

(56) References Cited

U.S. PATENT DOCUMENTS

2018/0078374 A1* 3/2018 Bae ...................... A61F 2/3094

FOREIGN PATENT DOCUMENTS

| | | | | |
|---|---|---|---|---|
| RU | 2111715 C1 * | 5/1998 | | |
| RU | 2195893 C2 * | 1/2003 | | |
| RU | 2456952 C1 * | 7/2012 | | |
| RU | 196831 U1 * | 3/2020 | ......... | A61B 17/8095 |
| WO | WO-2018081131 A1 * | 5/2018 | ........... | A61F 2/4455 |

* cited by examiner

*Primary Examiner* — Javier G Blanco
(74) *Attorney, Agent, or Firm* — Heslin Rothenberg Farley & Mesiti P.C.

(57) ABSTRACT

A surgical method surgical method includes collecting a set of patient data, identifying at least one significant point from the set of patient data, creating a surgical guide based on the at least one significant point and the patient data, and coupling the surgical guide with a calcaneum of a patient. The surgical method also includes performing at least one cut into the calcaneum using the surgical guide, wherein the at least one cut forms a recess in the calcaneum and defines a first calcaneal portion positioned substantially anteriorly from the recess and a second calcaneal portion positioned substantially posteriorly from the recess, shifting at least one of the first calcaneal portion and the second portion in a medial direction by placing an implant at least partially within the recess, and coupling the implant with the first calcaneal portion and the second calcaneal portion.

13 Claims, 7 Drawing Sheets

SYSTEMS AND METHODS FOR CONTROLLED FACET REPOSITIONING IN THE CALCANEUS

CROSS REFERENCE TO RELATED APPLICATION

This application claims priority benefit under 35 U.S.C. § 119(e) of U.S. Provisional Patent Application No. 63/170,174, filed Apr. 2, 2021, and entitled Systems and Methods For Controlled Facet Repositioning In The Calcaneus, which is incorporated herein by reference in its entirety.

TECHNICAL FIELD

The present disclosure relates to methods and systems for performing orthopedic procedures. The present disclosure relates to podiatric and orthopedic systems and methods related to osteotomy, arthroplasty, and repositioning of joints and/or musculoskeletal structures in the foot/ankle and/or procedures incorporating surrounding bones/soft tissue. More specifically, but not exclusively, the present disclosure relates to systems and methods, relating to calcaneal repositioning.

BACKGROUND OF THE INVENTION

Many currently available methods, implants, instrumentation, devices, and systems for addressing deformities and other conditions of the foot and ankle (e.g., flatfoot deformities, etc.) do not completely address the needs of patients. Additionally, many currently available methods, implants, instrumentation, devices, and systems, for addressing such deformities and conditions fail to account for properties anatomical properties and corresponding mechanical and kinematic movement patterns/capabilities.

SUMMARY

The present disclosure is directed toward systems and methods for controlled calcaneal facet repositioning.

A first aspect of the present disclosure is a surgical method. The surgical method includes collecting a set of patient data, identifying at least one significant point from the set of patient data, creating a surgical guide based on the at least one significant point and the patient data, and coupling the surgical guide with a calcaneum of a patient. The surgical method also includes performing at least one cut into the calcaneum using the surgical guide, wherein the at least one cut forms a recess in the calcaneum and defines a first calcaneal portion positioned substantially anteriorly from the recess and a second calcaneal portion positioned substantially posteriorly from the recess, shifting at least one of the first calcaneal portion and the second portion in a medial direction by placing an implant at least partially within the recess, and coupling the implant with the first calcaneal portion and the second calcaneal portion.

According to the first aspect of the present disclosure, the method also includes stabilizing one or more structures adjacent the calcaneum.

According to the first aspect of the present disclosure, the method also includes placing at least one implant trial within the recess to determine an appropriate size of the implant.

According to the first aspect of the present disclosure, the method also includes the at least one significant point having at least one of an anterior facet, a middle facet, and a posterior facet of the calcaneum.

According to the first aspect of the present disclosure, the method also includes the at least one cut extends at least partially between the anterior facet and the middle facet in a medial-lateral direction.

According to the first aspect of the present disclosure, the method also includes the at least one cut forming a substantially oblique angle with a coronal plane.

According to the first aspect of the present disclosure, the method also includes the surgical guide being configured to guide the at least one cut such that the at least one cut does not contact a medial cortex of the calcaneum.

According to the first aspect of the present disclosure, the method also includes the first calcaneal portion having an anterior facet and a middle facet of the calcaneum and the second calcaneal portion having a posterior facet of the calcaneum.

According to the first aspect of the present disclosure, the method also includes creating the implant based on the set of patient data.

According to the first aspect of the present disclosure, the method also includes the implant having a substantially wedge-shaped geometry.

According to the first aspect of the present disclosure, the method also includes the set of patient data having a first relationship between an anterior facet, a middle facet, and a posterior facet of the calcaneum.

According to the first aspect of the present disclosure, the method also includes placing the implant at least partially within the recess so as to establish a second relationship between the anterior facet, the middle facet, and the posterior facet, wherein the second relationship is different from the first relationship.

According to the first aspect of the present disclosure, the method also includes the at least one cut extending from a lateral portion of the calcaneum to a medial portion of the calcaneum.

According to the first aspect of the present disclosure, the method also includes the medial portion positioned further anteriorly than the lateral portion.

According to the first aspect of the present disclosure, the method also includes the lateral portion positioned further anteriorly than the medial portion.

According to the first aspect of the present disclosure, the method also includes rotating the second calcaneal portion substantially medially.

According to the first aspect of the present disclosure, the method also includes manipulating the first calcaneal portion such that the anterior facet is positioned substantially inferior relative to a head of a talus.

According to the first aspect of the present disclosure, the method also includes the set of patient data comprises computed tomography data.

A second aspect of the present disclosure is a surgical method. The method includes making a longitudinal incision on a lateral portion of a foot of a patient, identifying and preserving one or more soft tissue structures, and coupling a surgical guide with a calcaneum of the patient, wherein the surgical guide is created based on patient data. The surgical method also includes performing at least one cut in the calcaneum, wherein the at least one cut forms a recess in the calcaneum with a first portion of the calcaneum positioned anteriorly relative to the recess and a second portion of the calcaneum positioned posteriorly relative to the recess, and placing an implant within the recess such that at least one of the first portion of the calcaneum and the second portion of the calcaneum are repositioned in at least one plane.

A third aspect of the present disclosure is a surgical system. The surgical system includes a surgical guide configured to accommodate one or more significant points of a calcaneum of a patient, wherein the surgical guide is created based on patient data and configured to guide at least one cut so as to form a recess in the calcaneum, and an implant created based on the patient data, wherein the implant is configured to be inserted into the recess in the calcaneum so as to manipulate at least one of the one or more significant points of the calcaneum of the patient from a first position to a second position.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

DETAILED DESCRIPTION

Figure 1:
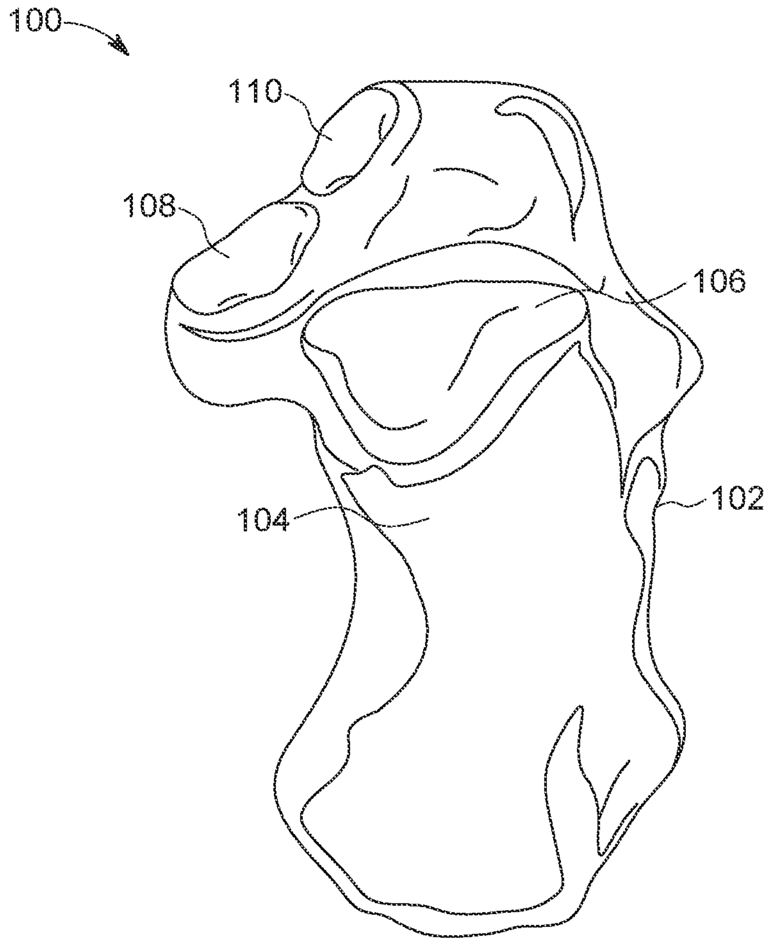
FIG. 1 is a top view of a calcaneum, in accordance with the present disclosure.

In this detailed description and the following claims, the words proximal, distal, anterior, or plantar, posterior, or dorsal, medial, lateral, superior, and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation, and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

The instruments, implants, systems, assemblies, and related methods for maintaining, correcting, and/or resurfacing joint surfaces of the present disclosure may be similar to, such as include at least one feature or aspect of, the implants, systems, assemblies and related methods disclosed U.S. Pat. No. 10,117,749, issued on Nov. 6, 2018; European Patent No. 3756626 issued on Dec. 30, 2020, European Patent Application No. 15770960.1A filed on Jul. 15, 2020; U.S. Provisional Patent Application No. 63/155,100 filed on Mar. 1, 2021; and U.S. Provisional Patent Application No. 63/167,965 filed on Mar. 30, 2021 which are all hereby incorporated herein by reference in their entireties.

Progressive collapsing foot deformity (PCFD) (similar to acquired adult flatfoot deformity, AAFD) is a chronic condition that is may be addressed with a lateral column lengthening (LCL) procedure. PCFD is also treated by numerous other surgical procedures (for example heel osteotomies, tendon transfers and/or lengthening, sinus tarsi implants, osteotomies of the hindfoot, midfoot, and forefoot, and various fusions), and treatment of the condition has become controversial. The lateral column of the foot includes the calcaneum, the cuboid, and the fourth and fifth metatarsals. LCL procedures typically involve performing an osteotomy of the lateral calcaneum and the subsequent placement of an implant (e.g., graft, wedge, etc.) within a void formed by the osteotomy. The implant is then secured within the void, with the objective of such a procedure being to provide correction for patients with flatfoot deformities. LCL procedures as currently performed frequently require other procedures to be performed in parallel with a calcaneal osteotomy, with up to five different procedures performed as a part of a single surgery. Techniques currently implemented in order to address LCL include various techniques, with two of the more common of these being the "Evans" and "Hintermann" techniques.

The Evans technique involves performing an osteotomy of the calcaneum in the area of the anterior and/or middle facets of the calcaneum and extending across the calcaneum in the medial-lateral direction substantially perpendicular to the coronal plane (and/or substantially perpendicular to the outer surfaces of the calcaneum). An implant is then placed within the void formed by the osteotomy with one or both of the portions of the calcaneum on opposite sides (anterior/posterior) of the void being manipulated by the implant being placed and secured within the void. Research has shown that the Evans technique has several drawbacks. For example, the Evans technique has shown to destabilize the anterior portion of the calcaneum, increase pressure to the calcaneum-cuboid joint, and damage one or more of the facets of the calcaneum (and subtalar joint) over time. The Evans technique has become associated with unfavorable outcomes as a function of the osteotomy contacting unintended structures. For example, the osteotomy of the Evans technique may include (inadvertently or otherwise) cutting through the middle facet of the subtalar joint (rather than cutting between the anterior and middle facets, where applicable), which may cause various conditions to develop, for example arthritis. In some instances, a saw implemented in an Evans procedure may pass across a medial border of the calcaneum thus damaging vital structures such as tendons, nerves, and blood vessels in the area. Other drawbacks of the Evans technique include lengthy recovery timelines to account for the unpredictability of the osteotomy (and structures contacted by said osteotomy) as well as the potential incorporation of multiple procedures within a single surgical procedure.

The Hintermann technique involves performing an osteotomy of the calcaneum in the area of the middle and/or posterior facets of the calcaneum and extending across the calcaneum in the medial-lateral direction (but may be made from a lateral-to-medial direction). An implant is then placed within the void formed by the osteotomy with one or both of the portions of the calcaneum on opposite sides (anterior/posterior) of the void being manipulated by the implant being placed and secured within the void. The osteotomy site and subsequent placement of the implant of the Hintermann technique is typically positioned posterior relative to the corresponding locations of the Evans technique. The Hintermann technique also has several drawbacks. For example, the Hintermann technique has shown to provide lesser correction than may be achieved by the Evans technique, and/or damage one or more of the facets of the calcaneum over time. The Hintermann technique commonly produces unfavorable outcomes, with one of such causes being the osteotomy contacting unintended structures. For example, the osteotomy of the Hintermann technique may include (inadvertently or otherwise) cutting through the middle facet of the calcaneum (rather than between the middle and posterior facets, where applicable) which may cause various conditions to develop, for example arthritis. In some instances, a saw may pass across a medial border of the calcaneum thus damaging vital structures such as tendons, nerves, and blood vessels in the area. Other drawbacks of the Hintermann technique include lengthy recovery timelines to account for the unpredictability of the osteotomy (and structures contacted by said osteotomy) as well as the potential incorporation of multiple procedures within a single surgical procedure.

Research has shown that a significant portion of the population may have irregular topography of the dorsal surface of the calcaneum. For example, research suggests that as much as 30% of the population may not have three defined facets, but rather a "fusion" of two of the three calcaneal facets that presents as an elongated facet with a footprint equal to or greater than approximately that of two distinguishable facets collectively. In some patients this may present as a continuity between the anterior and middle facets ("Type A") or a coalescence of the middle and posterior facets ("Type B"). Research also suggests that as much as 10% of the population may not have a defined posterior facet, but rather a coalescence of all three calcaneal facets that presents as a single facet with a footprint equal to or greater than approximately that of three distinguishable facets collectively ("Type C"). Additionally, other circumstances (e.g., deformity, trauma, etc.) may account for additional calcaneal topography that does not include three distinguishable facets. Accordingly, a more favorable surgical method (which may include implementation of various technologies, implants, etc.) with more favorable patient outcomes is desirable to address PCFD for all patients, including those fitting Types A, B, and C as defined herein.

Figure 2:
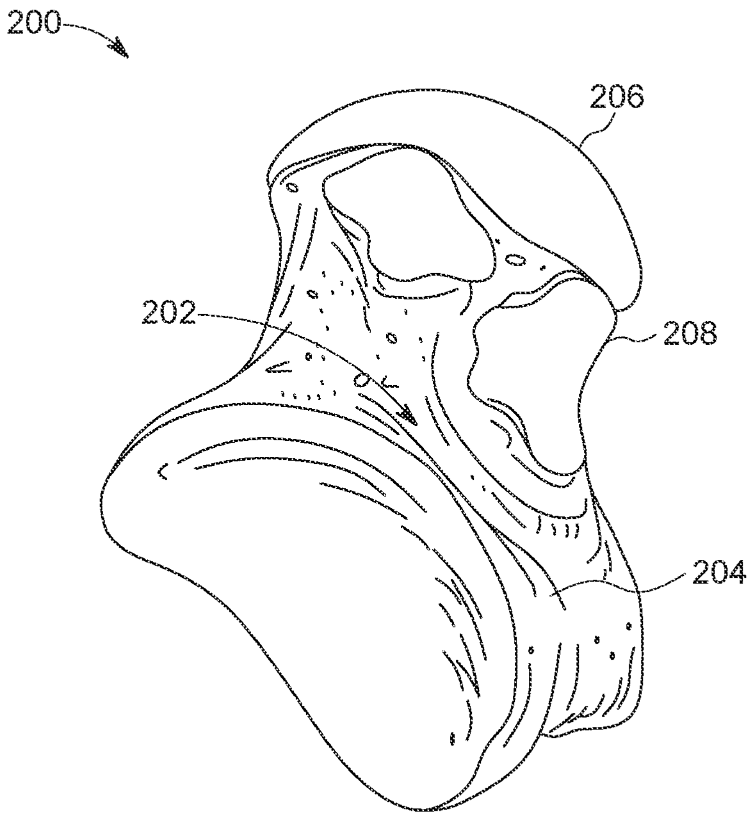
FIG. 2 is a bottom view of a talus, in accordance with the present disclosure.

Referring to the drawings, wherein like reference numerals are used to indicate like or analogous components throughout the several views, and with particular reference to FIGS. 1-2, there is illustrated an exemplary embodiment of a right calcaneum (e.g., calcaneus) 100 shown from a superior view and a right talus 200 shown from an inferior view. The calcaneum 100 and the talus 200 are bones of the foot/ankle and two bones of the subtalar joint which is disposed substantially inferior (e.g., distal) relative to the ankle. According to some research and corresponding literature, the subtalar joint may be considered two joints based on one or more facets disposed on the calcaneum 100, which are shown with reference to FIG. 1 and described subsequently herein. These two joints include a first joint (the subtalar joint) including the posterior facet of the calcaneum 100, and a second joint (the talocalcaneonavicular joint) including the middle and/or anterior facet as well as the talonavicular joint (including the talus 200 and the navicular (not shown). However, for the purpose of this disclosure the subtalar joint is considered to include at least the calcaneum 100 (including the posterior, middle, and anterior facets), the talus 200, and the soft tissue disposed therebetween. The subtalar joint, which is positioned superior relative to the calcaneum 100 and inferior relative to the talus 200 is configured to permit/enable movement. Typically, the subtalar joint permits movement that includes at least inversion and eversion of the foot, where inversion is defined as a movement that causes the soles of the feet to face inwards (e.g., in a medial direction) and eversion is defined as a movement that causes the soles of the feet to face outwards (e.g., laterally). Further, inversion and eversion can include external and internal rotation, respectively, of the talus 200 relative to (e.g., on) the calcaneum 100. The calcaneum 100 and the talus 200 (and components thereof) are shown and described herein so as to provide context for various steps of the subsequently disclosed method of performing arthroplasty of the subtalar joint. Furthermore, it should be noted that the calcaneum 100 and the talus 200 as shown correspond to such bones found in the right foot of a human and that the structures shown and described herein may have different sizing and/or orientation with respect to the left foot of a human (but can be reasonably assumed to be equal and opposite) in the medial-lateral directions. It should be understood that the calcaneum 100 and the talus 200 may not be representative of the geometry of such bones of any/all humans/patients but are shown herein to be representative of the general geometry and features of the bones. For example, trauma, bone deformity, arthritis and other conditions can alter the geometry of such bones. As referred to herein, arthroplasty is defined as surgical reconstruction and/or joint replacement of a joint (in the context of this disclosure, the subtalar joint). It should be known that both the calcaneum 100 and the talus 200 may include other geometric features, interfaces with other portions of anatomy, and articulations in addition to those discussed herein.

The calcaneum 100 is shown to include a body 102 which includes a top surface 104. The top surface 104 of the calcaneum 100 may substantially include a superior surface of the calcaneum 100 and form at least a portion of an inferior portion and/or defining surface of the subtalar joint. In some aspects, the top surface 104 interfaces with cartilage positioned between the calcaneum 100 and the talus 200 (e.g., the subtalar joint) that may be removed in performing a subtalar joint arthroplasty. In some aspects, the top surface 104 may become one of two interfacing surfaces of a subtalar joint after arthroplasty is performed (e.g., a surface that interfaces with a subtalar joint implant). The top surface 104 may have various geometries depending on the patient and the condition of the calcaneum 100 (e.g., trauma, arthritis, deformity, etc.). As shown, the top surface 104 includes a posterior facet 106, a middle facet 108, and an anterior facet 110 as shown in FIG. 1. In some aspects, one or more of the posterior facet 106, the middle facet 108 and the anterior facet 110 may be less distinguishable than shown on the calcaneum 100 in FIG. 1. For example, in some aspects the middle facet 108 and the anterior facet 110 may be positioned closer to one another than shown in FIG. 1 such that the middle facet 108 and the anterior facet 110 overlap and/or abut one another (e.g., there is not a gap positioned anterior-lateral the middle facet 108). In some aspects, the calcaneum body 102, the posterior facet 206, the middle facet 108, the anterior facet 110 (as well as other components of the top surface 204 and the calcaneum 100) may be referenced as anthropometric markers (e.g., landscape markers, identifiers, etc.) in order to analyze movement and/or other kinematic properties of the calcaneum 100 and/or surrounding joints. It should also be understood that one or more events or conditions (e.g., trauma, arthritis, deformity, etc.) may alter the calcaneum 100 of a patient such that one or more of the features described has an altered geometry, is damaged, or is not present on the calcaneum 100 of a patient.

The talus 200 is shown to include a body 102 and a bottom surface 104. The top surface 204 of the talus 200 may substantially include an inferior surface of the talus 200 and form at least a portion of a superior portion and/or defining surface of the subtalar joint. In some aspects, the bottom surface 204 interfaces with cartilage positioned between the calcaneum 100 and the talus 200 (e.g., the subtalar joint) that may be removed in performing a subtalar joint arthroplasty. In performing arthroplasty of the subtalar joint, at least a portion of subcortical bone may be removed in order to place one or more components of an implant so as to promote maximum stability of the joint as well as other surrounding joints and structures. In some aspects, the bottom surface 204 may become one of two interfacing surfaces of a subtalar joint after arthroplasty is performed (e.g., a surface that interfaces with a subtalar joint implant). The bottom surface 204 may have various geometries depending on the patient and the condition of the calcaneum 100 (e.g., trauma, arthritis, deformity, etc.). The talus 200 is further shown to include a talar head 206 positioned at an anterior portion of the talus 200, with a talar neck 208 extending between the body 202 and the talar head 206. In some aspects, the talar body 202, the talar head 206, and the talar neck 208 (as well as other components of the bottom surface 204 and the talus 200) may be referenced as anthropometric markers (e.g., landscape markers, identifiers, etc.) in order to analyze movement and/or other kinematic properties of the talus 200 and/or surrounding joints.

Figure 3:
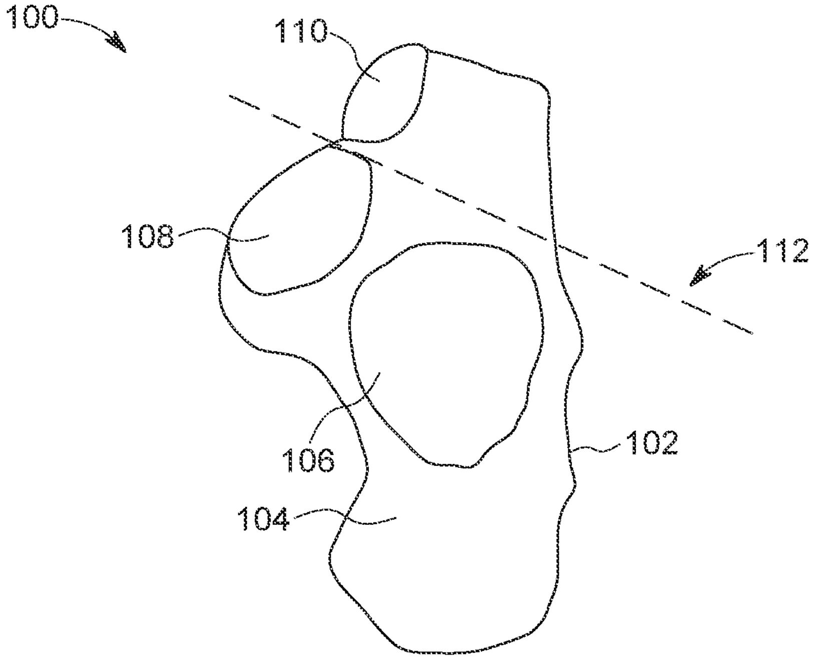
FIG. 3 is top schematic view of a calcaneum showing a potential cut line for a surgical method, in accordance with the present disclosure.

Referring now to FIGS. 3-5B, the calcaneum 100 and associated components are shown as it relates to a controlled facet relocation of one or more facets of the calcaneum 100 through a procedure guided by the surgical method/methods shown and described herein. FIG. 3 is shown to include a cut line 112 extending from a first point on the medial side of the calcaneum 100 between the middle facet 108 and the anterior facet 110, across (shown as across in the two-dimensional FIG. 3, but in practice at least partially through at least a portion of) the calcaneum 100, to a second point on the lateral side of the calcaneum. As shown in FIG. 3, the cut line 112 forms a substantially oblique angle with both the coronal plane and the sagittal/parasagittal planes. The cut line 112 is shown to be representative of at least a portion of a plane along which an osteotomy cut may be made in implementing the surgical procedure described herein. In some aspects, the cut line 112 may correspond to a cut that is made at a substantially oblique angle with the vertical, for example the upper-most portion of the cut is positioned anterior relative to the lower-most portion of the cut slot, or similar medial-lateral variation. It should be understood that the identification of "first point" and "second point" with reference to the cut line 112 are not indicative of any chronology of the cut that may be made along the cut line 112 (e.g., the cut may begin at a medial point along the cut line 112, a lateral point, etc.).

Figure 8:
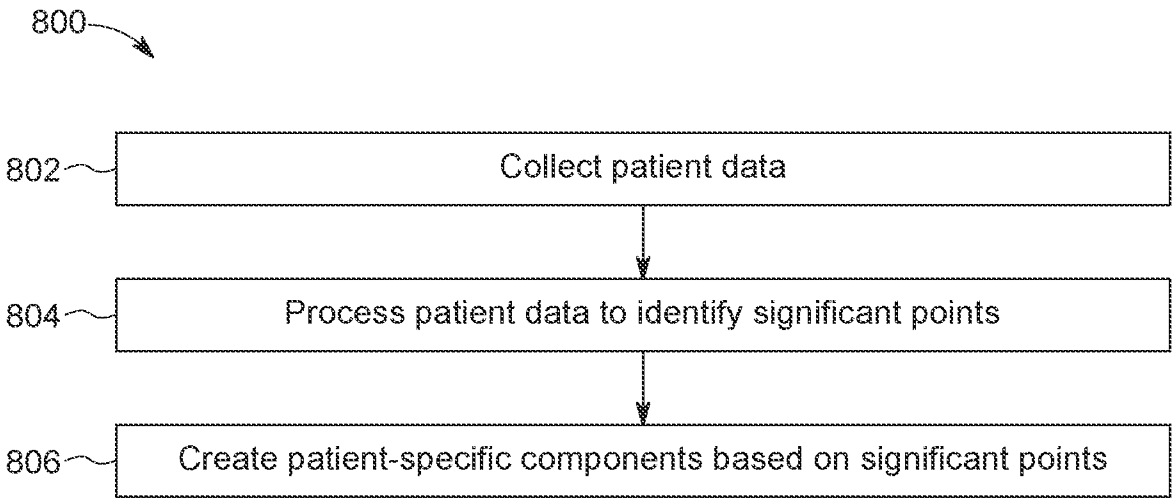
FIG. 8 is a flowchart showing a process of a surgical method, in accordance with the present disclosure.

The cut line 112 may be determined based on data collected from a patient using one or more imaging technologies such as that shown and described herein with reference to FIG. 8. As shown, the cut line 112 is configured to establish a first portion of the calcaneum 100 (e.g., the anterior-most portion) and a second portion of the calcaneum 100 (e.g., the posterior-most portion). The cut line 112 is configured such that the anterior facet 110 is positioned entirely on the first portion of the calcaneum 100, while the posterior facet 106 and the middle facet 108 are positioned entirely on the second portion of the calcaneum 100. In some aspects, a patient may have significant points (e.g., anatomical features, axes and angles thereof, etc. and locations thereof other than that shown in the exemplary calcaneum 100 shown in FIGS. 3-5B, and the cut line 112 may a) be positioned so as to minimally contact one or more of the middle facet 108 and anterior facet 110, orb) have different first and/or second points (and a different line therebetween) so as to reflect a cut planned to avoid contacting the middle facet 108 and the anterior facet 110. If the cut line 112 overlaps one or more of the middle facet 108 and the anterior facet 110, the first portion of the calcaneum 100 may include at least a major portion of the anterior facet 110 (e.g., more than half) while the second portion of the calcaneum may include at least a major portion of the posterior facet 106 and/or the middle facet 108. In some aspect, the cut line 112 may be determined based on alternate points that are identified/located based on the patient data collected. For example, in some aspects the cut line 112 may be at least partially dependent on the position of the talar head 206 of the talus 200. In other aspects, the cut line 112 may depend at least partially on geometric properties and/or relationships between anatomical points. For example, in some aspects the cut line 112 may be determined based on the location of one or more geometric axes identified on one or more significant points (e.g., an axis of each facet, an axis connecting or relating the position of multiple facets, various angles that incorporate various axes, one or more sphered that correspond to the topography of the surface of the calcaneum, etc.).

Figure 4:
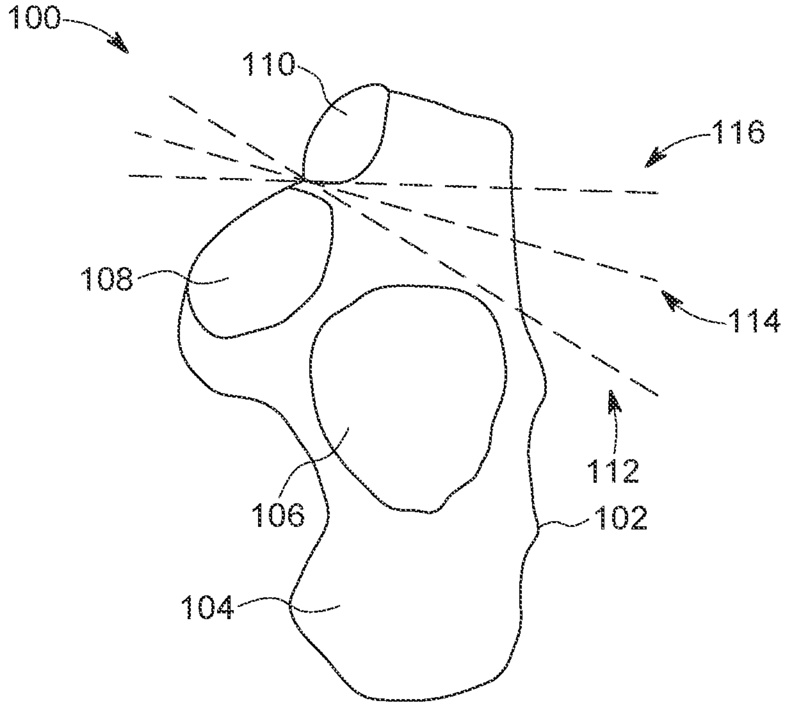
FIG. 4 is a top schematic view of a calcaneum showing potential alternate cut lines for a surgical method from that shown in FIG. 3, in accordance with the present disclosure.

FIG. 4 is shown to include a second cut line 114 and a third cut line 116 adjacent the cut line 112 for reference. In some aspects, one or more factors of the anatomy of a patient (e.g., chronic conditions, deformity, facet configuration and condition, etc.) may result in a determination (as a function of analyzing/processing patient data as shown and described with reference to FIG. 8) that the second cut line 114, the third cut line 116, or an alternate cut line not shown may provide the optimal outcome for the patient. In some aspects, such an optimal outcome may correspond to current facet position relative to desired/ideal facet position. As shown, both the second cut line 114 and the third cut line 116 avoid contacting the middle facet 108 and/or the anterior facet 110. As shown, the cut line 112, the second cut line 114, and the third cut line 116 include similar first points (medial points) on the medial portion of the calcaneum 100, but different lateral points on the lateral portion of the calcaneum 100. For example, the second cut line 114 includes a second point (lateral point) positioned anterior relative to the second point of the first cut line 112. Accordingly, on the calcaneum 100 as shown (which is an exemplary calcaneum and is not intended to be representative of any/all calcanei of patients) an osteotomy performed on the cut line 114 would produce a smaller first portion (anterior portion) of the calcaneum 100 and a larger second portion (posterior portion) of the calcaneum 100 relative to an osteotomy performed along the cut line 112. Further, an osteotomy performed at the cut line 114 may result in less surface area of the calcaneum 100 at the osteotomy site than that of the cut line 112 (as the cut line 112 is more oblique (e.g., closer to 45-degrees from the coronal plane) and thus corresponds to greater surface area of the calcaneum 100 along the cut line. In some aspects, increased surface area may be advantageous and conducive to greater distribution of forces in the anterior-posterior direction as well as more fusion/union with an implant placed at the osteotomy site. Similarly, the third cut line 116 includes a second point (lateral point) positioned anterior that of the second cut line 114. Accordingly, on the calcaneum 100 as shown an osteotomy performed on the third cut line 116 would produce a smaller first portion (anterior portion) of the calcaneum 100 and a larger second portion (posterior portion of the calcaneum 100 relative to an osteotomy performed along the second cut line 114. Further, an osteotomy performed at the third cut line 116 may result in less surface area of the calcaneum 100 at the osteotomy site than that of the second cut line 114. As discussed previously, in some aspects greater surface area may be preferable and accordingly, a cut line the same as and/or similar to that of the cut line 112 may be determined to be preferable. Conversely, in some aspects lesser surface area may be preferable and accordingly, a cut line the same as and/or similar to that of the third cut line 116 may be determined to be preferable.

Figure 5A:
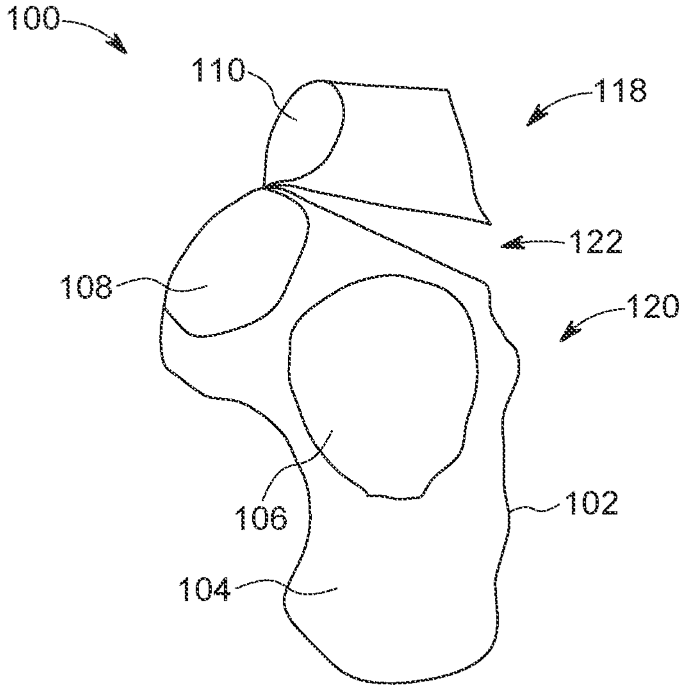
FIG. 5A is a top schematic view of a calcaneum showing an osteotomy site of a surgical method, in accordance with the present disclosure.
Figure 5B:
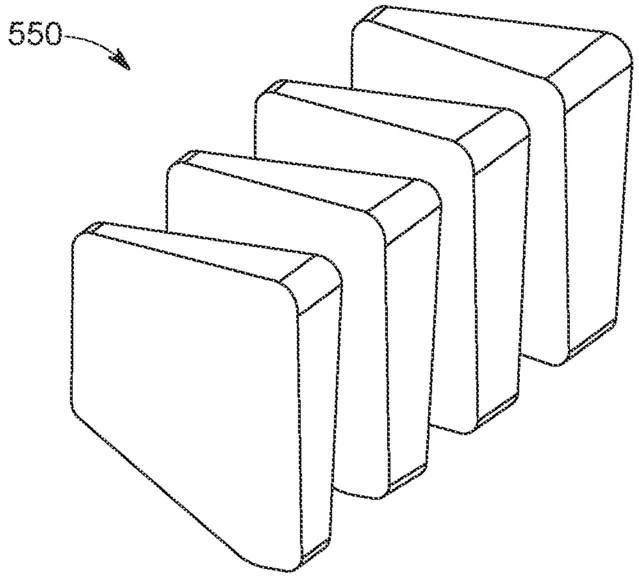
FIG. 5B is a perspective view of various implants for use at an osteotomy site, in accordance with the present disclosure.

Referring now to FIG. 5A, a recess (e.g., void, etc.) 122 is shown at a site that corresponds to the cut line 112 as shown in FIGS. 3-4. As shown in FIG. 5, the recess 122 is exemplary and not intended to be exactly to scale of a recess resultant of an osteotomy performed along the cut line 112 as shown in FIGS. 3-4. The recess 122 is shown to be substantially defined anteriorly in superior to inferior (vertical) and medial to lateral (horizontal) directions by the first portion (anterior portion) of the calcaneum 100, and substantially defined posteriorly in superior to inferior and medial to lateral directions by the second portion of the calcaneum 100. As shown, and depending on the frame of reference, one or both of the first and second portions of the calcaneum 100 have been shifted (e.g., rotated, pivoted, repositioned, etc.) in a substantial medial direction. In some aspects such as that shown in FIG. 5A, the first portion of the calcaneum 100 may be shifted/pivoted about a substantially posterior-medial most point in a substantially counterclockwise direction when viewed from a superior perspective. Conversely, in FIG. 5A the second portion of the calcaneum 100 may be shifted/pivoted by applying one or more forces about one or more planes about a substantially anterior-medial most point in a substantially clockwise direction when viewed from a superior perspective. Accordingly, one or a combination of both of the aforementioned shifts of the first and/or second portions of the calcaneum 100 provides lateral access to the recess 122 which is shown to have a substantially triangular geometry (or triangular prism/wedge-shaped geometry when viewed three-dimensionally). In some aspects, the first and/or second portions of the calcaneum 100 may be shifted/pivoted by applying one or more forces about one or more planes to provide access to the recess 122. Alternatively, in some aspects the shift/pivot of the first and/or second portions of the calcaneum 100 may be driven by the insertion of an implant within the recess 122, for example one or more of a set of implants 550 as shown in FIG. 5B. It should be noted that the calcaneum 100 is a right calcaneum and the subsequent positioning, shifting, pivoting and other manipulation as described herein is described relative to a right calcaneum. It should be noted that for implementing the surgical method shown and described herein on a left calcaneum of a patient, various directions may be reversed (e.g., clockwise becomes counterclockwise, etc.).

In some aspects, it may be determined that the first portion of the calcaneum 100 (and, accordingly, the anterior facet 110, needs to be shifted medially and/or rotated/pivoted in a substantially counterclockwise direction. For example, processing and analysis of patient data may indicate that the talar head 206 is neutrally positioned but the anterior facet 110 is positioned substantially laterally and/or posteriorly the desired position of the anterior facet 110 (which may be substantially inferior relative to the talar head 206). Accordingly, the second portion of the calcaneum 100 may be kept static with the first portion of the calcaneum 100 either manipulated as described previously such that the recess 122 may receive an implant of the set of implants 550 therein, or an implant of the set of implants 550 is inserted and placed at least partially within the recess 122 so as to drive the first portion of the calcaneum 100 (and thus the anterior facet 110) to the desired position substantially inferior relative to the talar head 206. In another example, processing and analysis of patient data may indicate that the anterior facet 110 (and accordingly, the first portion of the calcaneum 100) are in a desired position substantially inferior relative to the talar head 206, but the second portion of the calcaneum 100 is biased laterally and/or anteriorly from a desired position. Accordingly, the first portion of the calcaneum 100 may be kept static with the second portion of the calcaneum 100 either manipulated as described previously such that the recess 122 may receive an implant of the set of implants 550 therein to support the manipulated position of the second portion of the calcaneum 100, or an implant of the series of implants 550 may be placed at least partially within the recess 122 so as to drive the second portion of the calcaneum 100 (and thus the posterior facet 106 and the middle facet 108) to the desired position.

The series of implants 550 as shown include four implants of varying dimensions with a symmetrical (e.g., at least one line of symmetry) and substantially wedge-shaped geometry. In some aspects, one or more wedges the same as and/or similar to those of the series of implants 550 may be placed within the recess 122 and evaluated relative to the resultant position(s) of the first and/or second portions of the calcaneum (and portions thereof). In some aspects, a physician may implement one or more implant trials having dimensions the same as and/or similar to those of the implants within a set, with said implant trials placed within the recess 122. Based on the performance of one or more implant trials, and implant from a set of implants such as those of the set of implants 550 may be selected and implanted within the recess 122. As shown in the set of implants 550, in some aspects various bone graft materials may be implemented as implants, while in other aspects metal or other biocompatible components may be implemented. In some aspects, a custom implant having a custom geometry may be placed and implanted within the recess 122, with said custom implant created based on desired positions of one or more anatomical components as determined by the patient data collected. Once an implant has been appropriately placed, the implant may be secured within the recess 122 so as to control motion in all three anatomical planes (including rotational movement) by implementing one or more coupling means, for example plating and various fasteners (which may couple with the first and second portions of the calcaneum 100 and span the recess 122 thus retaining the implant therein).

The dimensions and geometry of the implant required by the recess 122 may vary depending on the cut line determined for and implemented in the osteotomy. For example, with reference to FIG. 4, an implant to be placed in a recess 122 corresponding to a cut made along the cut line 112 may require a greater hypotenuse surface (e.g., a surface corresponding with the hypotenuse of a wedge a substantially right-triangle geometry) than that of an implant placed in a recess 122 corresponding to a cut made along the third cut line 116. In some aspects, the dimensions of an implant to be placed within the recess 122 may correspond (e.g., via one or more mathematical relationships) to the length of the cut line implemented in the osteotomy as well as various dimensions of the calcaneum 100 (e.g., height).

Figure 6:
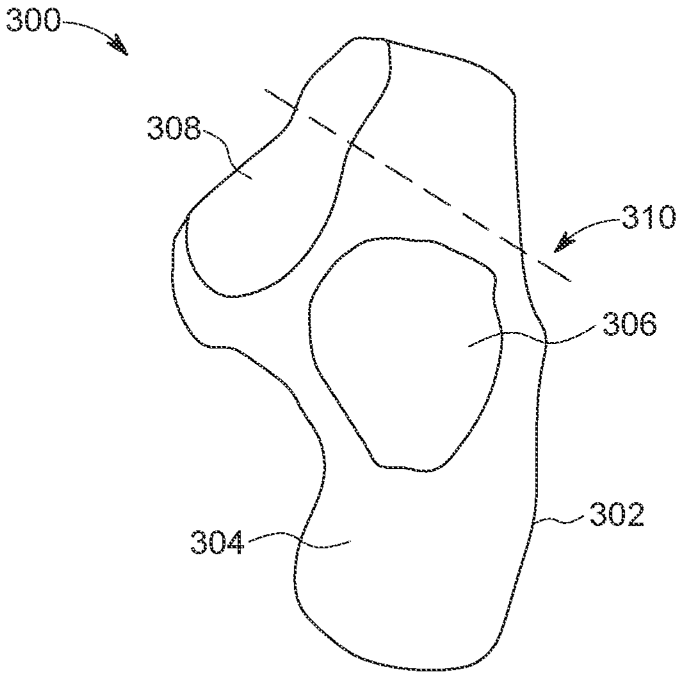
FIG. 6 is top schematic view of a calcaneum with an alternate anatomy showing a potential cut line for a surgical method, in accordance with the present disclosure.
Figure 7:
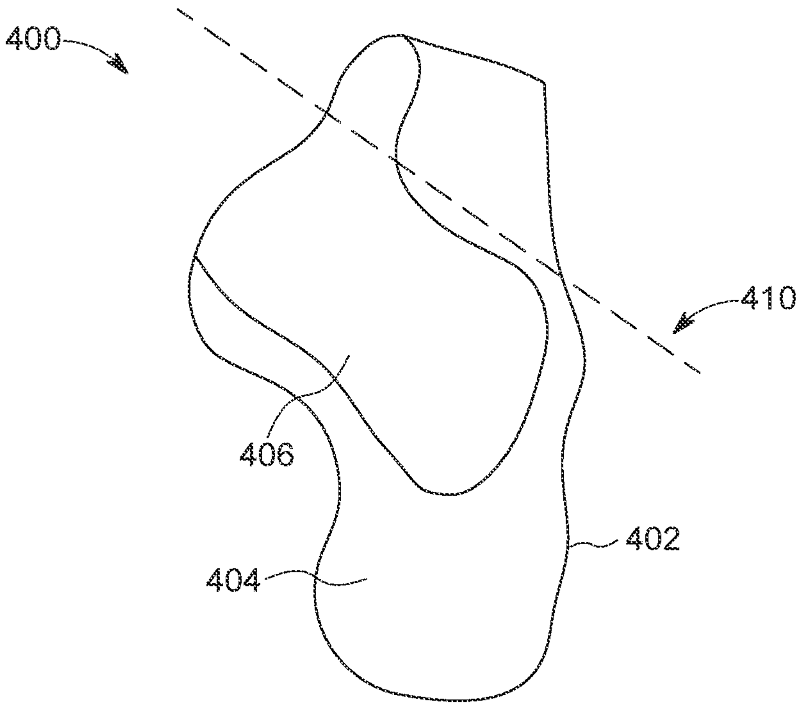
FIG. 7 is a top schematic view of a calcaneum with an additional alternate anatomy showing a potential cut line for a surgical method, in accordance with the present disclosure.

Referring now to FIGS. 6-7, a pair of irregular calcanei 300 and 400 are shown, respectively. The calcaneum 300 corresponds to the Type A patient as discussed previously, where the middle facet and anterior facet (shown previously as 108, 110) are not distinguishable from one another and the calcaneum 300 instead includes a body 302 having a top (superior) surface 304 that includes a posterior facet 306 and a continuous facet 308. As shown, the continuous facet 308 has a footprint that corresponds to approximately at least the footprint of the middle facet 108 and the anterior facet 110 as shown and described previously. In determining a cut line 310, patient date may be processed/analyzed to determine a cut line that contacts the continuous facet 308 along a similar plane to the cut lines shown and described previously. In some aspects, the cut line 310 may be determined such that a first (anterior) portion of the calcaneum 300 would contain bone mass and/or volume and/or topography similar to that shown in the first portion of the calcaneum 100 as shown and described with reference to FIG. 5A. Performing an osteotomy cut along the line 310 may also result in a second (posterior) portion of the calcaneum 300 including bone mass and/or volume and/or topography similar to that shown in the second portion of the calcaneum 100 as shown and described with reference to FIG. 5A. Accordingly, one or both of the first and second portions of the calcaneum 300 may be manipulated in a manner the same as and/or similar to that shown and described previously with reference to FIG. 5A. An implant may then also be placed and secured as shown and described with reference to FIG. 5A.

The calcaneum 400 corresponds to the Type C patient as discussed previously, where the posterior facet, middle facet, and anterior facet (shown previously as 106, 108, 110) are not distinguishable from one another and the calcaneum 400 instead includes a body 402 having a top (superior) surface 404 that includes a continuous facet 406. As shown, the continuous facet 406 has a footprint that corresponds to approximately at least the footprint of the posterior facet 106, the middle facet 108, and the anterior facet 110 as shown and described previously. In determining a cut line 410, patient date may be processed/analyzed to determine a cut line that contacts the continuous facet 406 along a similar plane to the cut lines shown and described previously. In some aspects, the cut line 410 may be determined such that a first (anterior) portion of the calcaneum 400 would contain bone mass and/or volume and/or topography similar to that shown in the first portion of the calcaneum 100 as shown and described with reference to FIG. 5A. Performing an osteotomy cut along the line 410 may also result in a second (posterior) portion of the calcaneum 400 including bone mass and/or volume and/or topography similar to that shown in the second portion of the calcaneum 100 as shown and described with reference to FIG. 5A. Accordingly, one or both of the first and second portions of the calcaneum 400 may be manipulated in a manner the same as and/or similar to that shown and described previously with reference to FIG. 5A. An implant may then also be placed and secured as shown and described with reference to FIG. 5A.

Referring now to FIG. 8, a flowchart is shown for a process 800 of preoperative planning for a patient-specific procedure, according to an exemplary embodiment. As shown, the process 800 may be applied to a patient with PCFD or other similar flatfoot deformity for which an osteotomy technique such as those shown and described previously herein may be favorable. In some aspects, one or more steps of the process 800 may be applicable to various other orthopedic procedures. The process 800 may be performed in advance of a procedure (or multiple procedures) being performed on a patient. The process 800 may be performed in order to facilitate the implementation of one or more of the surgical methods shown and described previously herein (e.g., to facilitate various osteotomy cut lines, calcaneal topographies, etc.). The process 800 may be performed by physicians/surgeons and/or other medical professionals in advance of a surgical procedure being performed (for example, a surgical procedure following the surgical method shown and described herein). The steps of the process 800 may be performed in an alternate order than that shown with reference to FIG. 8. Further, the steps of the process 800 may be repeated, skipped, include one or more subprocesses, or have additional steps added in order to complete the process 800. It should also be understood that one or more of the steps of the process 800 may be performed by or include the implementation of one or more robotic surgery techniques or technologies.

The process 800 is shown to include a step 802 collecting patient data, according to the exemplary method shown and described with reference to FIG. 8. In some aspects, the step 802 may be performed once and/or may be repeated. The step 802 may include incorporating one or more imaging techniques in order to collect patient data, for example computed tomography (CT), magnetic resonance imaging (MRI), fluoroscopy, X-ray, or other imaging methods. Such imaging may be focused on the calcaneum 100 and components thereof, for example the posterior facet 106, the middle facet 108, and the anterior facet 110, as well as other structures of the calcaneum 100 and/or other surrounding structures.

The process 800 is shown to include a step 804 processing patient data to identify significant points, according to the exemplary method shown and described with reference to FIG. 8. The step 804 may include identifying one or more of the significant points of the calcaneum 100 and/or surrounding structures (e.g., talus, cuboid, etc.) shown and described with reference to FIGS. 1-7, for example the posterior facet 106, the middle facet 108, the anterior facet 110, the medial cortex (not shown), the talar head 206, the talar neck 208, etc. In some aspects the step 804 may be dependent on one or more of the previous steps of the process 800 in that the points that may be identifiable on the calcaneum 100 and/or surrounding structures may be dependent on the patient data collected (e.g., CT, MM, X-ray, etc.). In some aspects, the step 802 may further include a determination that the step 802 will be repeated in order to collect additional and/or different patient data through the implementation various imaging methods, for example. As discussed herein previously, in some aspects one or more anatomical components of the calcaneum 100 and/or surrounding structures may not be present or may not be identifiable (e.g., trauma, degeneration, deformity, Type A, B, or C, etc.). In some aspects, the step 804 may include identifying one or more of the aforementioned points with respect to one or more of the other aforementioned points (or other anatomical points entirely). For example, if the middle facet 108 and the anterior facet 110 abut one another or are continuous, the posterior facet 108 may be identified as a point and furthermore may be identified (e.g., measured, mapped, etc.) with respect to points of the calcaneum 100 other than the middle facet 108 and the anterior facet 110 or with respect to points of the talus 200, for example the talar head 206. The step 804 may also include the identification and measurement/estimation of one or more angles associated with the calcaneum 100, the talus 200, or other significant points/structures, for example the Angle of Gissane. Other geometric points that may be identified may include one or more axes of the posterior facet 106, the middle facet 108, and/or the anterior facet 110. Additionally, the step 804 may include identifying current positions of one or more of the posterior facet 106, the middle facet 108, and/or the anterior facet 110 and subsequently identifying desired positioned of the posterior facet 106, the middle facet 108, and/or the anterior facet 110 (with the desired position being post-operative). The step 804 may also include the identification and/or analysis of the current position of various points and the corresponding stability of the calcaneum 100 (e.g., the anterior facet 110 relative to the talar head 206). Accordingly, a desired position of one or more points may be determined relative to the current position so as to increase the stability of the calcaneum 100 (e.g., the anterior facet 110 having a desired position substantially inferior relative to the talar head 206). Soft tissue points and other structures may also be identified including the soft tissue structures mentioned previously as well other structures, for example the sural nerve, the peroneal tendons, superficial peroneal nerve, etc.

The step 804 may also include the identification of an ideal osteotomy location on the calcaneum 100 and determining a corresponding cut (e.g., cut line, cut path, etc.). In some aspects, such an ideal osteotomy location may be the same as and/or similar to one or more of the osteotomy locations and/or cut lines as shown and described previously herein. In determining an ideal osteotomy location, one or more of the identified points/structures and/or current/desired positions may be considered. For example, upon identification of the middle facet 108 and the anterior facet 110 (in the instance that both structures are distinguishable and the patient is not one of Types A, B, or C), an osteotomy location may be identified including a cut line extending from a medial point between the middle facet 108 and the anterior facet 110, across the calcaneum 100 in the medial-lateral direction at an angle that is substantially oblique to the coronal plane, to a lateral point on the lateral surface of the calcaneum 100. Thus, the osteotomy does not contact the middle facet 108 and thus lessens the risk of arthritic development in the patient. In another example, upon identification that the middle facet 108 and the anterior facet 110 are continuous (e.g., Type A), the ideal osteotomy location may be determined to be at a substantially central point on the continuous facet (when viewed from a superior perspective) (e.g., so as to create a quasi-middle facet and a quasi-anterior facet) of the calcaneum 100. The ideal osteotomy location may also include depth parameters, for example the cut may have a depth in the calcaneum 100 lesser than that of the medial cortex. In some aspects, other osteotomy locations may be identified and may incorporate one or more other facets or anatomical components identified from the patient data collected in the step 802.

The process 800 is shown to include a step 806 creating patient-specific components based on significant points, according to the exemplary method shown and described with reference to FIG. 8. The patient specific components created in the step 806 may include one or more surgical guides (e.g., cut guides) and/or one or more implants. In some aspects, the surgical guide(s) may be configured to guide a cut based on an osteotomy location including a cut line that has been identified as described in the step 804 as described previously. The surgical guide(s) may be configured to interface with one or more anatomic features of the calcaneum 100 and/or other surrounding structures. The surgical guide(s) may also include one or more features configured to facilitate coupling of the surgical guide(s) with the calcaneum 100 (or other structures), for example releasable coupling via one or more stabilization wires (e.g., k-wires, olive wires, etc.). The surgical guide(s) may also include at least one slot configured to receive a cutting instrument (e.g., reciprocating saw) therethrough so as to guide one or more cuts, for example along a cut line the same as and/or similar to the cut line 112, the second cut line 114, and/or the third cut line 116. Accordingly, the surgical guide(s) may further guide the cut in a superior/inferior direction so as to prevent the medial cortex from being contacted. The surgical guide(s) may be generated (e.g., created) by 3-D printing a model generated based on the patient data collected in the step 802. Additionally, the surgical guide(s) may include additional features, for example a depth stop. The depth stop may be configured based on a length of a cut to be made, with said length determined based on the patient data collected. For example, if a 75 mm saw blade is to be used to make a cut with a depth of 35 mm, the surgical guide(s) may include a depth stop of 40 m with said depth stop protruding from the surgical guide(s) in a direction substantially opposite that of the calcaneum 100. Accordingly, only 35 mm of the saw blade would be permitting to pass through the slot of the surgical guide(s) so as to prevent the saw from making a cut deeper than the desired 35 mm.

The step 806 may also include generating (e.g., creating) one or more implants configured to occupy the recess 122. In some aspects, the implant may have a substantially wedge-shaped or other symmetrical geometry (e.g., has at least one line of symmetry) with consistent properties (e.g., height, density, etc.) across a width or along a length of the implant. However, in some aspects the implant may have an asymmetrical geometry and/or may have one or more properties (such as but not limited to those mentioned previously) that are inconsistent across a width or along a length of the implant. The implant may also be configured to occupy some and/or all of the recess 122. In some aspects, the implant may be configured to have at least one flat surface that, when the implant is positioned within the recess 122 as desired, creates a substantially smooth (e.g., flush) surface along an exterior surface of the calcaneum 100.

Figure 9:
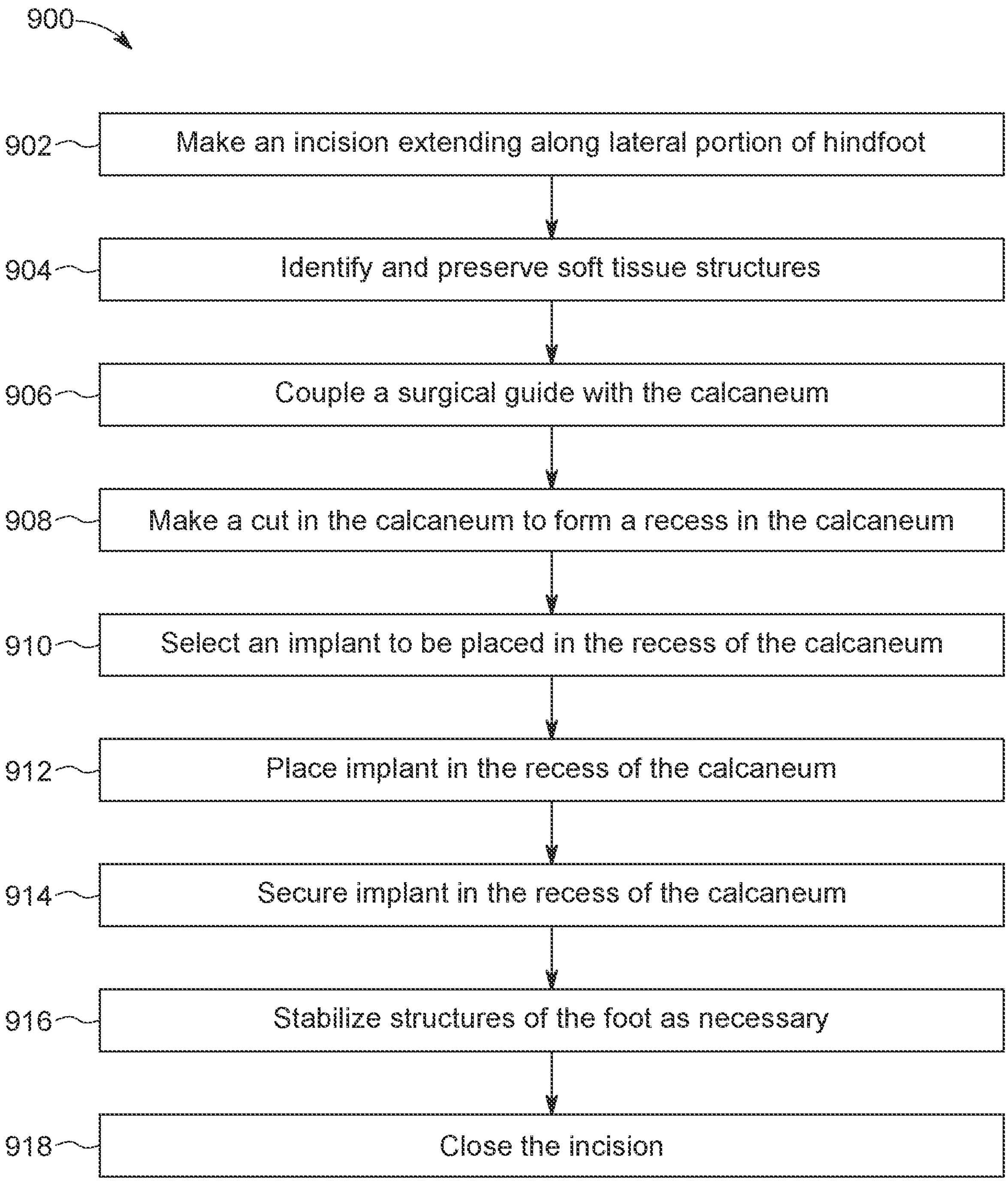
FIG. 9 is a flowchart showing a subsequent process to that shown in FIG. 8 for a surgical method; in accordance with the present disclosure.

Referring now to FIG. 9, a flowchart is shown for a process 900 of a surgical method. As shown, the process 900 is representative of at least a portion of a surgical method for addressing deformities of the hindfoot that includes performing a facet arthroplasty (e.g., controlled facet repositioning). The following description of the process 900 will largely include references to the calcaneum 100 as shown in FIGS. 1 and 3-5B and described previously herein. Such description is not limiting to the calcaneal configuration of the calcaneum 100 and may be adapted as discussed previously and discussed further here to follow and applied to calcanei with alternate configurations, for example that of the calcanei 300, 400 as shown and described previously. The process 900 may include implementing one or more of the same and/or similar concepts to those discussed previously with reference to FIGS. 1-7. For example, the process 900 may include performing an osteotomy along a cut line, where depending on the anatomy of the patient, the cut line may be the same as and/or similar to that of the cut line 112, the second cut line 114, the third cut line 116, the cut line 310, and/or the cut line 410. Further, one or more implants the same as and/or similar to those shown and described with reference to FIG. 5B (as well as other implants contemplated herein) may be implemented in performing the process 900 and steps thereof. Additionally, the process 900 may be performed in series (e.g., after, with the prior being requisite steps) with the process 800 as shown and described with reference to FIG. 8. The process 900 and the steps thereof are not limiting, which is to say that the process 900 may be performed as shown in FIG. 9 and may also have additional steps implemented variously throughout the process 900. In performing the process 900 one or more steps thereof may be skipped, repeated, or performed in a chronology other than that shown in FIG. 900. Additionally, one or more physicians or other medical personnel may be involved in performing one or more steps of the method 900. It should also be understood that one or more of the steps of the process 900 may be performed by or include the implementation of one or more robotic surgery techniques or technologies.

The process 900 is shown to include a step 902 making an incision extending along a lateral portion of the hindfoot, according to the exemplary method shown and described with reference to FIG. 9. In some aspects the incision of the step 902 may be initiated adjacent the distal fibula and continue along a lateral portion of the hindfoot toward the forefoot in a substantially anterior direction. The terminal point of the incision of the step 902 may depend on the discretion of a physician relative to the anatomy of the patient. For example, if a patient has one or more severe deformities (including and/or in addition to PCFD) a physician may extend the incision of the step 902. In some aspects, the incision in the step 902 may be dependent on the sizing of a surgical guide and/or implant that a physician intends to implement in a procedure. Further, the length of the incision of the step 902 may also depend on the estimated location of a cut line for an osteotomy, with said incision created so as to ensure that the aforementioned cut line will be accessible via said incision.

The process 900 is shown to include a step 904 identifying and preserving soft tissue structures, according to the exemplary method shown and described with reference to FIG. 9. In some aspects, one or more steps of the process 800 may have identified one or more soft tissue structures and/or other structures of the lateral portion of the foot. For example, the processing and analysis of the patient data may have included identification and mapping of the peroneal tendons and the sural nerve as well as other soft tissue or nervous system components positioned adjacent the calcaneum 100. In some aspects, the step 904 may include the implementation of one or more instruments to identify, manipulate, and/or reposition one or more of the aforementioned structures. For example, an instrument with a blunt distal portion may be implemented to perform a blunt dissection and access the calcaneum 100.

The process 900 is shown to include a step 906 coupling a surgical guide with the calcaneum, according to the exemplary method shown and described with reference to FIG. 9. The surgical guide of the step 906 may correspond to the patient-specific surgical guide(s) contemplated previously with reference to the step 806 of the process 800. In some aspects the step 906 may include coupling multiple surgical guides and/or components thereof with the calcaneum 100 on a lateral surface thereof, but henceforward will be discussed as a singular surgical guide. The surgical guide of the step 906 may include one or more geometric components configured to interface with one or more corresponding geometric features of the calcaneum 100 of the patient (on at least the lateral surface of the calcaneum 100). Accordingly, the surgical guide may also include one or more cut slots disposed thereon the surgical guide configured to receive one or more cutting instruments as discussed previously. The surgical guide may be coupled with the calcaneum 100 such that the one or more cut slots may align with one or more cut lines, for example cut lines the same as the cut line 112 or other cut lines shown and described previously. The step 906 may include implementing one or more stabilization wires configured to be received by one or more components of the surgical guide so as to facilitate releasable coupling with the calcaneum 100.

The process 900 is shown to include a step 908 making a cut in the calcaneum to form a recess in the calcaneum, according to the exemplary method shown and described with reference to FIG. 9. The cut in the calcaneum 100 may be made by inserting a cutting instrument (e.g., reciprocating saw blade or another cutting instrument) through a slot of the surgical guide that was coupled with the calcaneum 100 in the step 906. The step 908 may include making said cut along a cut line (for example, the cut line 112) where said cut line corresponds to a plane (including depth in the medial-lateral direction and depth in the superior-inferior direction so as to prevent the cutting instrument from making unintended contact with significant structures. For example, the surgical guide may correspond with the cut line so as to prevent a reciprocating saw blade from contacting the middle facet 108, the anterior facet 110, the medial cortex (not shown), or other adjacent structures commonly contacted in LCL procedures that may be conducive to degeneration and other conditions of the foot. In some aspects, the medial cortex may be preserved so as to function as a “hinge” of the calcaneum 100. Additionally, the surgical guide may have a depth stop to prevent the cutting instrument from being inserted too far into and through a slot of the surgical guide (and thus further prevent contact with unintended structures). The cut made in the calcaneum 100 in the step 908 may form the recess 122 (e.g., void) such as that shown in FIG. 5A or other similar recess that corresponds with the cut line 112 (or similar).

The process 900 is shown to include a step 910 selecting an implant to be placed in the recess of the calcaneum, according to the exemplary method shown and described with reference to FIG. 9. The step 910 may include placing one or more trial implants from a set of trial implants (where each trial implant has incrementally different dimensions and/or geometry) within the recess 122 so as to determine the appropriate size for such an implant. In some aspects, a set of implants such as the set of implants 550 may be provided with the set of trial implants with an implant that corresponds to each trial implant. Accordingly, once the appropriate implant size has been determined by iterative placement of one or more trial implants, the corresponding implant from the set of implants may be placed within the recess 122. In some aspects, one or more patient-specific implants may be generated as discussed previously and, upon creating of the recess 122 in the step 908, the patient specific implant is placed within the recess 122. In some aspects, implant sizing may be based on desired position/repositioning of one or more anatomical structures of the calcaneum 100 relative to other surrounding structures in one or more planes. For example, as described previously implants/implant trials may be placed within the recess 122 until an implant size adequately positions the anterior facet 110 (and the first portion of the calcaneum 100) substantially inferior relative the talar head 206 (thus manipulating the calcaneum 100 from a less stable configuration to a more stable configuration). In another example, implants/implant trials may be placed within the recess 122 until an implant size adequately shifts the posterior facet 106 and the middle facet 108 (and the second portion of the calcaneum 100) substantially medially from a less stable configuration to a more stable configuration. In some aspects, the implant may be selected such that the first and/or second portion of the calcaneum 100 is manipulated in one or more planes by placement of the implant within the recess 122. In some aspects, the implant may be placed and selected such that the first (anterior) portion of the calcaneum 100 is shifted medially such that the anterior-most point of the calcaneum 100 does not move further in the anterior direction. Similarly, in some aspects the implant may be placed and selected such that the second (posterior) portion of the calcaneum 100 may be shifted medially such that the posterior-most point of the calcaneum 100 does not move further in the posterior direction. In some aspects, the implant size may be selected such that one or more surfaces of the implant disposed within the recess 122 contact opposing surfaces of the recess 122. Accordingly, such contact may be supplemented with one or more biologic substances (e.g., bone void filler, bone cement, etc.) so as to facilitate fusion/union of the first and second portions of the calcaneum 100 with the implant.

The process 900 is shown to include a step 912 placing an implant in the recess of the calcaneum, according to the exemplary method shown and described with reference to FIG. 9. As the appropriately sized implant selected in the step 910 is placed within the recess 112, one or both of the first and second portions of the calcaneum may be manipulated (e.g., driven/biased in one or more directions by a force applied to the implant to position the implant at least partially within the recess). In some aspects, one or both of the first and second portions of the calcaneum may have one or more forces applied in one or more planes to bias said components as discussed with reference to the step 910, with said force/forces providing access to the recess 122 such that the implant may be placed within the recess and thus prevent movement of the first and second portions of the calcaneum to the previous, preoperative position. In some aspects, the implant may be aligned with the cut line 112 such that a force may be applied to the implant in a plane substantially parallel to that of the cut line 112 so as to drive the implant at least partially into the recess 122 and thereby shifting/biasing one or both of the first and second portions of the calcaneum 100.

The process 900 is shown to include a step 914 securing an implant in the recess of the calcaneum, according to the exemplary method shown and described with reference to FIG. 9. Once the implant is placed at least partially within the recess 122, one or more securing mechanisms are implemented in order to retain the implant within the recess 122 and thus maintain the correction provided by the implant. In some aspects, various securing mechanisms may be used including one or more of plates/plating, screws/fasteners, staples, or other securing mechanisms. In some aspects, the implant may be secured within the recess 122 such that the lateral most portion/portions of the implant form a smooth surface (e.g., sit flush) with the lateral-most surface of the calcaneum 100. In some aspects, a securing mechanism (for example a plate or staple) may be coupled via screws/fasteners with the first and second portions of the calcaneum such that the securing mechanism spans at least a portion of the lateral-most portion of the recess 122 so as to apply a force substantially parallel to that of the cut line 112 and thereby retain the implant within the recess.

The process 900 is shown to include a step 916 stabilizing structures of the foot, according to the exemplary method shown and described with reference to FIG. 9. Following the securing of the implant within the recess in the step 914, a physician and/or other medical personnel may evaluate other structures of the foot to evaluate stability. In some aspects a physician may determine that the increased stability of the calcaneum exposes existing instability at another portion of the foot. For example, a physician may determine that the Lapidus joint lacks stability and perform a fusion of the first metatarsal and the medial cuneiform in order to increase the collective stability of the foot. Further to the previous example, a physician may also determine that the overall stability of the foot would be increased by placement of a Cotton wedge and, accordingly, places such a wedge. Additional structures of the foot beyond those discussed herein may also be evaluated by a physician for stability.

The process 900 is shown to include a step 918 closing the incision, according to the exemplary method shown and described with reference to FIG. 9. Once a physician has determined that the foot (including the calcaneum) has sufficient stability, said physician may replace any soft tissue, nervous, or other structures on the lateral portion of the foot that were repositioned or bluntly dissected in order to access the calcaneum 100. In some aspects, one or more of such structures may have been damaged and if such is the case, a physician may perform such a repair in the step 918. Once all structures are determined to be sufficiently intact and properly positioned, a physician may close the incision created in the step 902.

It should be understood that the process 900 may be modified over the course of performing the process 900. For example, one or more steps of the process 900 may be skipped, repeated, modified, performed out of the order shown, or replaced with an alternate step. It should also be understood that the steps of the process 900 correspond to at least a portion of a surgical method for addressing deformity of the hindfoot and, as such, may be modified according to the anatomy of the patient. While various anatomical configurations are shown and discussed herein, alternate anatomical configurations may require that the process 900 be modified or otherwise adapted in order to accommodate say alternate anatomical configurations.

It should be noted that, in some aspects, the system and surgical methods shown and described herein may be adapted and applied to the talus 200 of a patient. For example, the processes 800, 900 may be implemented for the talus 200 of a patient. The process 800, for example, may include collecting imaging data of the talus 200 of a patient, processing said data, and then generating/creating one or more surgical guides configured to guide an osteotomy cut along a predetermined cut line (similar to the determination of the cut line 112 and/or other cut lines discussed herein, where said cut lines are determined based on the identification of one or more significant anatomical points). Further, the process 800 may include generating/creating one or more implants that correspond to said osteotomy and cut line such that said implant(s) provide a predetermined correction (e.g., manipulate one or more portions of the talus 200 from a first position to a second desired position). The process 900 may be modified to accommodate the talus 200 as well, for example an incision may be made on the medial or lateral portion of the foot (with the location of the incision depending on anatomical structures, soft tissue, etc.) and identifying and repositioning soft tissue and other structures adjacent the talus 200. Further, the process 900 may be modified such that the surgical guide(s) are coupled with the talus 200 on medial and/or lateral portions thereof such that one or more cuts may be made (along the predetermined cut lines, as described above) to perform an osteotomy. One or more implants and/or trial implants may then be placed within a recess created by the osteotomy cut (similar to the recess 122), with an implant selected based on said implant providing a desired correction (e.g., one or more components shifted to/maintained in a desired position by the presence of the implant within the recess). The process 900 may also be modified to use a securing element similar to those described previously so as to retain the implant within the recess and thus maintain the desired correction. The stability of the foot may also be evaluated as described in the step 916 of the process 900. The aforementioned soft tissue and other adjacent structures may then be repositioned, with the incision closed after said structures have been determined to be correctly positioned.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A surgical method, comprising:

collecting a set of patient data;

identifying at least one significant point from the set of patient data;

creating a surgical guide based on the at least one significant point and the patient data;

making a longitudinal incision on a lateral portion of a foot of a patient;

identifying and preserving one or more soft tissue structures;

coupling the surgical guide to a calcaneum of a patient;

performing at least one cut into the calcaneum using the surgical guide, wherein the at least one cut forms a recess in the calcaneum with the recess defined by a first calcaneal portion positioned substantially anteriorly from the recess and a second calcaneal portion positioned substantially posteriorly from the recess;

shifting at least one of the first calcaneal portion and the second calcaneal portion in at least one plane by placing an implant at least partially within the recess; and securing the implant within the recess, wherein the at least one significant point comprises at least one of an anterior facet, a middle facet, and a posterior facet of the calcaneum, wherein the at least one cut extends at least partially between the anterior facet and the posterior facet in a medial-lateral direction, wherein the first calcaneal portion comprises the anterior facet of the calcaneum, and the second calcaneal portion comprises the posterior facet of the calcaneum, wherein the implant comprises a substantially wedge-shaped geometry.

2. The method of claim 1, further comprising stabilizing one or more structures adjacent the calcaneum.

3. The method of claim 1, further comprising placing at least one implant trial within the recess to determine an appropriate size of the implant.

4. The method of claim 1, wherein the at least one cut extends at least partially between the anterior facet and the middle facet in a medial-lateral direction.

5. The method of claim 1, wherein the at least one cut forms a substantially oblique angle with a coronal plane.

6. The method of claim 1, wherein the first calcaneal portion further comprises the middle facet of the calcaneum.

7. The method of claim 1, further comprising creating the implant based on the set of patient data.

8. The method of claim 1, wherein the set of patient data comprises a first relationship between the anterior facet, the middle facet, and the posterior facet of the calcaneum.

9. The method of claim 8, wherein placing the implant at least partially within the recess produces a second relationship between the anterior facet, the middle facet, and the posterior facet, wherein the second relationship is different from the first relationship.

10. The method of claim 1, wherein the at least one cut extends from a lateral portion of the calcaneum to a medial portion of the calcaneum.

11. The method of claim 10, wherein the medial portion is positioned further anteriorly than the lateral portion.

12. The method of claim 10, wherein the lateral portion is positioned further anteriorly than the medial portion.

13. The method of claim 1, further comprising rotating the second calcaneal portion substantially medially.

* * * * *